United States Patent
Hollett (10) Patent No.: US 9,480,818 B2
(45) Date of Patent: Nov. 1, 2016

(54) ROTATABLE TIP FOR ENDOSCOPIC MEDICAL DEVICES

(75) Inventor: Andrew K. Hollett, Waltham, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 785 days.

(21) Appl. No.: 13/571,181

(22) Filed: Aug. 9, 2012

(65) Prior Publication Data

US 2013/0053766 A1   Feb. 28, 2013

Related U.S. Application Data

(60) Provisional application No. 61/526,055, filed on Aug. 22, 2011.

(51) Int. Cl.
*A61M 25/00* (2006.01)
*A61M 25/09* (2006.01)
*A61M 25/01* (2006.01)

(52) U.S. Cl.
CPC ..... *A61M 25/0069* (2013.01); *A61M 25/0074* (2013.01); *A61M 25/0147* (2013.01); *A61M 25/09041* (2013.01); *A61M 25/0127* (2013.01); *A61M 2025/018* (2013.01)

(58) Field of Classification Search
CPC ............... A61M 25/0067; A61M 2025/0063; A61M 25/01; A61M 25/0133; A61M 2025/018; A61M 25/0069; A61M 25/0074; A61M 25/0127; A61M 25/0147; A61M 25/09041; A61M 2025/015; A61B 2019/2211; A61B 2017/003; A61B 19/22; A61B 1/018; A61B 5/042; A61B 2017/00292; A61B 2017/0034; A61B 2017/32003
USPC ................................................ 604/95.04, 528
See application file for complete search history.

(56) References Cited

U.S. PATENT DOCUMENTS

| | | | |
|---|---|---|---|
| 5,114,403 A * | 5/1992 | Clarke et al. | 604/95.04 |
| 5,772,609 A | 6/1998 | Nguyen et al. | |
| 6,139,510 A | 10/2000 | Palermo | |
| 6,235,026 B1 * | 5/2001 | Smith | 606/46 |
| 7,758,591 B2 | 7/2010 | Griego et al. | |
| 2003/0109861 A1 * | 6/2003 | Shimada | 606/14 |
| 2011/0224575 A1 * | 9/2011 | Carrillo et al. | 600/566 |

* cited by examiner

*Primary Examiner* — Nathan R Price
*Assistant Examiner* — Weng Lee
(74) *Attorney, Agent, or Firm* — Seager, Tufte & Wickhem, LLP (57) ABSTRACT

Medical devices as well as methods for making and using medical devices are disclosed. An example medical device may include an elongate catheter shaft having a distal end. A tip member may be rotatably coupled to the distal end of the catheter shaft. The tip member may have a groove formed therein. The groove may extend along a portion of the circumference of the tip member. A control member may be coupled to the catheter shaft. The control member may be configured to engage the helical groove and rotate the tip member.

13 Claims, 10 Drawing Sheets

ROTATABLE TIP FOR ENDOSCOPIC MEDICAL DEVICES

CROSS-REFERENCE TO RELATED APPLICATIONS

This application claims priority under 35 U.S.C. §119 to U.S. Provisional Application Ser. No. 61/526,055, filed Aug. 22, 2011, the entirety of which is incorporated herein by reference.

TECHNICAL FIELD

The present disclosure pertains to medical devices, and methods for manufacturing medical devices. More particularly, the present disclosure pertains to endoscopic catheters with a rotatable tip.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

The invention provides design, material, manufacturing method, and use alternatives for medical devices (including endoscopic catheters, guidewire, and the like) and/or medical device assemblies. An example medical device may include an elongate catheter shaft having a distal end. A tip member may be rotatably coupled to the distal end of the catheter shaft. The tip member may have a groove, for example a helical groove, formed therein. The groove may extend along a portion of the circumference of the tip member. A control member may be coupled to the catheter shaft. The control member may be configured to engage the groove and rotate the tip member.

An example endoscopic medical device assembly may include an endoscopic catheter. A guidewire may be disposed within the catheter. The guidewire may have an outer surface with a raised portion disposed thereon. The catheter may have a deflecting structure disposed therein that is configured to engage the guidewire so that the guidewire rotates relative to the catheter when the guidewire is extended distally relative to the catheter.

An example method for performing a medical procedure may include providing a catheter. The catheter may include an elongate catheter shaft having a distal end and a tip member rotatably coupled to the distal end of the catheter shaft. The tip member may have a groove formed therein. The catheter may also include a control wire that is engaged with the groove and configured rotate the tip member. The method may also include advancing the catheter through a body lumen to a position adjacent to a target region and rotating the tip member relative to the catheter shaft by actuating the control wire.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

A wide variety of biliary, endoscopic, and/or endosurgical procedures have been developed for making medical treatments, diagnoses, and images of areas along the biliary tract and/or the pancreatic tract. For the purposes of this disclosure, the "biliary tract" and/or the "pancreatic tract" are understood to include various components of the digestive system and include, for example, the various ducts of the biliary tree between the liver and the duodenum as well as the various ducts between the pancreas and the duodenum. Numerous endoscopic and/or endosurgical devices have been developed for making medical treatments, diagnoses, and images of areas along the biliary and pancreatic tracts. Some of these device and/or procedures include sphincterotomes, biliary catheters, biliary guidewires, biliary stent delivery systems, drainage of the bile duct, splinting of the bile duct during healing, providing bile duct patency in a stricture or past a stone, and the like. In general, these devices are guided to the biliary and/or pancreatic tract by an endoscope (and/or a duodenoscope) that is disposed in the duodenum. Once positioned, various interventions can be performed depending on the needs of the patient and the type of device utilized. Other locations and/or uses are also contemplated for the systems disclosed herein including, for example, urinary tract interventions and/or urological interventions, gynecological interventions, etc.

During procedures along the biliary tract, it may be desirable to selectively access the common bile duct or pancreatic duct selectively. While some devices such as sphincterotomes may include features that allow the tip of the device to be flexed, the degree of control over the tip of endoscopic and/or biliary device may be limited. Consequently, even when the tip of an endoscopic device is altered or flexed, the clinician may still end up cannulating the wrong target site (e.g., the pancreatic duct is cannulated when the common bile duct was targeted), which may be undesirable and could result in inflammation and/or undue patient trauma.

Disclosed herein are a number of medical devices that may have improved control over cannulation. At least some of the devices disclosed herein include catheters and/or guidewires that are can be manipulated (e.g., rotated) so that the devices can reliably cannulate a selected target site.

Figure 1:
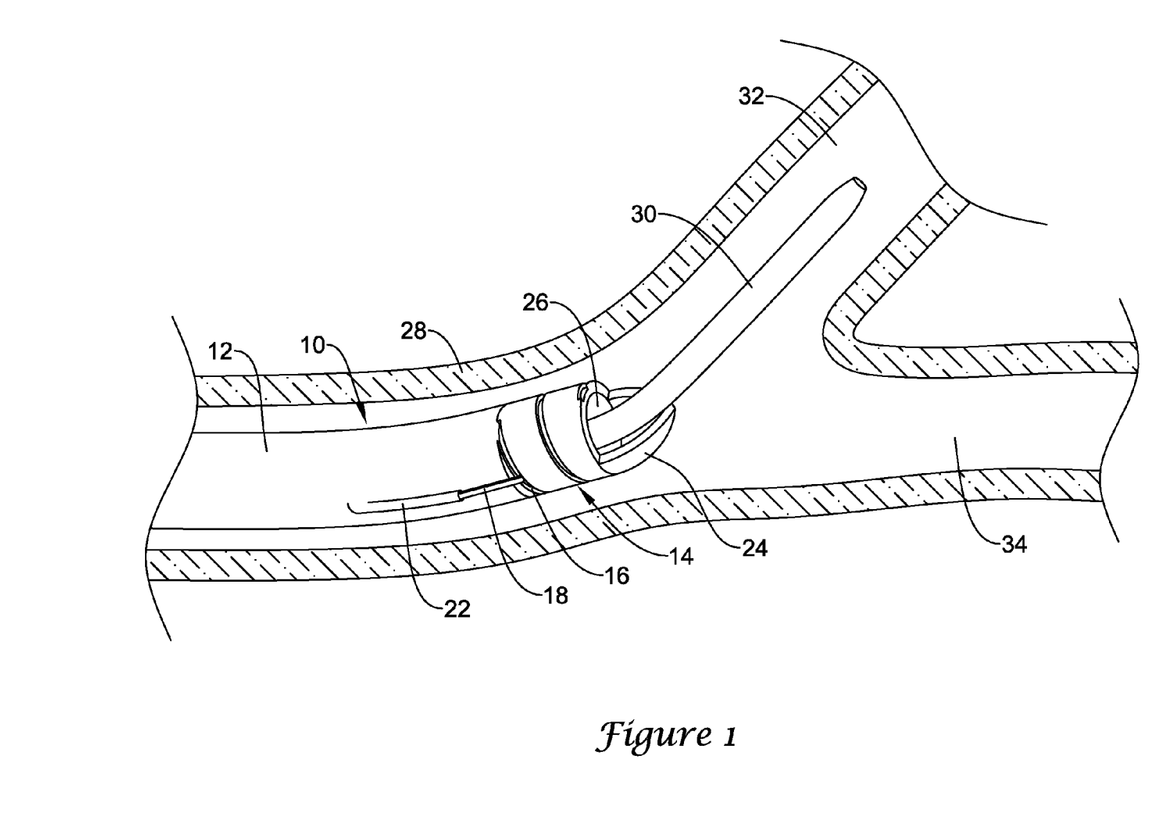
FIG. 1 is a partial cross-sectional side view of an example medical device disposed in a body lumen.

FIG. 1 is a partial cross-sectional side view of an example medical device 10. In general, medical device 10 may be an endoscopic medical device. In other words, medical device 10 may be configured for use with an endoscope. In this example, medical device 10 takes the form of an endoscopic catheter. Other devices are contemplated including but not limited to, for example, sphincterotomes, biliary catheters, biliary guidewires, biliary stent delivery systems. Catheter 10 may include a catheter shaft 12 having a tip member 14 coupled thereto. Tip member 14 is configured to be rotatable relative to catheter shaft 12. This feature desirably allows a clinician to alter the positioning and/or orientation of tip member 14 during an intervention. This may allow the clinician to selectively point or orient tip member 14 in a variety of different directions. Because of this, tip member 14 may be utilized to provide greater control and more accurate placement of devices during, for example, cannulation of structures along the biliary tree and/or the GI tract.

Tip member 14 may be coupled to catheter shaft 12 in any suitable manner. This may include any number of different types of bonds that permit rotation of tip member 14 relative to catheter shaft 12. For example, a threaded connection may be utilized to secure tip member 14 to catheter shaft 12. Other connections are also contemplated including swivel-type joints, ball joints, bearing joints or the like. In one example embodiment, tip member 14 or catheter shaft 12 includes an enlarged end portion that is configured to fit within a corresponding opening on the opposing structure. In such embodiments, the enlarged portion may be press-fit into the opening to secure tip member 14 with catheter shaft 12. These are just examples as several other types of connections are contemplated for joining tip member 14 to catheter shaft 12. In general, tip member 14 is configured to rotate, at least partially, about the axis of the catheter shaft 12. The tip may connect to the outside of the catheter, the inside of the catheter, or a combination of both.

Tip member 14 may include a structural feature that can be manipulated or otherwise used to cause rotation of tip member 14. For example, tip member 14 may have a groove such as a helical groove 16 formed therein. In some embodiments, helical groove 16 is a continuous helical groove carved into a portion of the exterior of tip member 14. Other configurations, however, are contemplated. For example, helical groove 16 may be carved into an interior surface of tip member 14, which may be located interior or exterior to tip member 14. In other embodiments, helical groove 16 is formed within a wall surface of tip member 14. This later embodiment may reduce exposure of groove 16 to the anatomy. These are just examples.

In some cases, the device may require only a limited rotation for orientation purposes, such as only one full rotation or several full rotations about the axis of the tip member 14. In some cases, this relatively small amount of rotation may be achieved using a pull wire in a groove having a limited length. In other cases, the catheter itself may be slightly elastic (e.g., like some polymers) and may be torqueable, so that the tip member 14 could be eliminated.

Other variations are also contemplated including variations to the length of groove 16 (e.g., less than one revolution about tip member 14 to several revolutions about tip member 14), the pitch or angle of groove 16 (e.g., nearly upright to nearly axially oriented), the number of grooves 16 (e.g., 1, 2, 3, 4, or more), the groove pattern or other variations.

Tip member 14 may have an angled tip 24, which in turn defines an angled opening 26 at the distal end of catheter shaft 12. As the name suggests, angled tip 24 and angled opening 26 are oriented at an angle relative to the longitudinal axis of catheter shaft 12. Because of this, angled tip 24 and/or opening 26 may function as a guide or ramp that directs a device extending therethrough in a selected direction depending on the orientation of angled tip and/or opening 26. Angled tip 24 is designed so that when catheter 10 is advanced through a body lumen 28 and body lumen 28 comes to a junction of, for example, a first duct or pathway 32 (e.g., the common bile duct) and a second duct or pathway 34 (e.g., the pancreatic duct), angled tip 24 can be rotated so as to selectively point toward the desired pathway 32/34 so that the desired pathway 32/34 may be efficiently cannulated. For example, a device 30 (e.g., a catheter, guidewire, etc.) may be passed through the catheter shaft 12 to a position adjacent to the junction of pathways 32/34. Tip member 14 can then be rotated so that the angled opening 26 of angled tip 24 is pointed in the direction of the desired pathway (e.g., either pathway 32 or pathway 34) and then device 30 can be advanced through opening 26 into the desired pathway, as selected. Because tip member 14 may be selectively oriented in a particular direction, it may be possible for cannulation to be performed without the need of a guidewire disposed across the target site or otherwise maintaining access to a particular target. This may desirably simplify a number of interventions. Angled tip may also be controllable in angle, either by passive means dependent on the geometry of the tip, or by active means such as a pull wire. In other words, tip member 14 may be steerable.

The manner in which tip member 14 is rotated may vary. In at least some embodiments, a control member 18 may be coupled to helical groove 16. Control member 18 may take the form of a control wire that engages groove 16. In general, control member 18 may be made from a material with sufficient column strength so that control member 18 can be urged distally so as to rotate tip member 14 without bucking. The precise engagement mechanism between control member 18 and groove 16 may vary. For example, an end portion of control member 18 may be disposed within and be slidable within groove 16. In order for control member 18 to remain engaged with groove 16, the distal end may be enlarged, flattened, sled-shaped (e.g., like a boat hull), have a ball-shaped tip, and so forth, so that a mechanical interlock can be formed between control member 18 and groove 16 (e.g., groove 16 may have an outer rim that can mechanically hold the enlarged end of control member 18 therein). Other mechanisms may also be utilized to hold control member 18 in engagement with groove 16, if desired.

Figure 2:
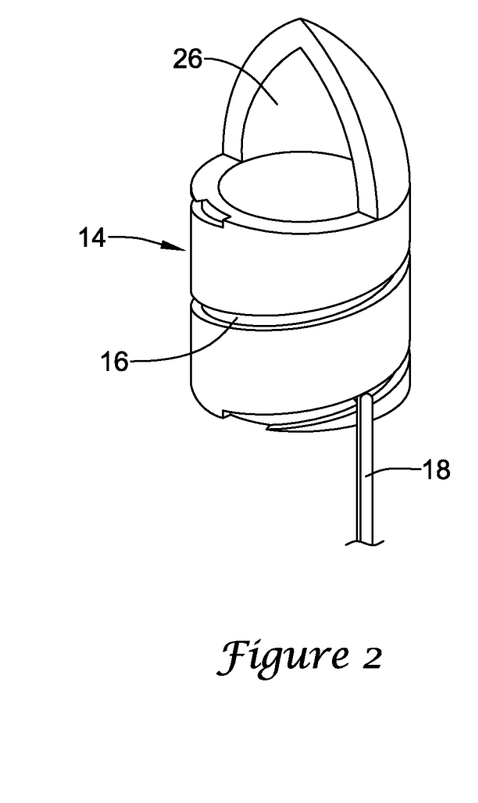
FIG. 2 is a perspective view of a tip member for use with an example medical device.
Figure 3:
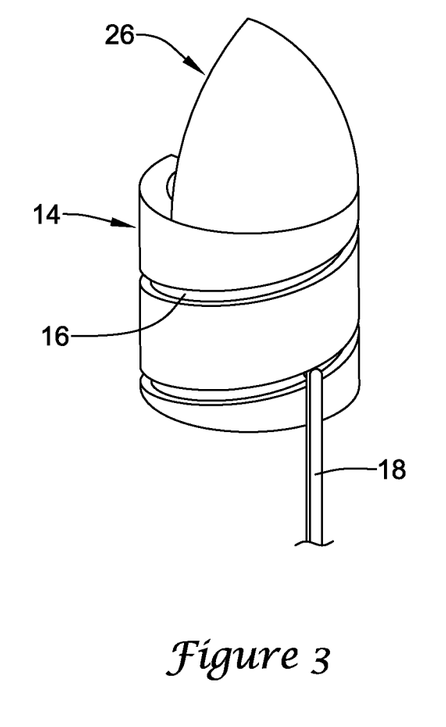
FIG. 3 is a perspective view of the tip member shown in FIG. 2 where the tip member has been rotated.

To rotate tip member 14, control member 18 may be advanced distally and/or retracted proximally. In doing so, control member 18 exerts a force in either the distal or proximal direction onto groove 16 (and, thus, tip member 14), which rotates tip member 14. As tip member 14 rotates, control member 18 advances within groove 16. An example of the relative rotation of tip member 14 and positioning of control member 18 during rotation is illustrated in FIGS. 2-3. For example, FIG. 2 illustrates control member 18 disposed at a first location within groove 16. As control member 18 is urged distally, control member 18 tracks along groove 16 to a second location within groove 16 and rotates tip member 14 as shown in FIG. 3. In doing so, opening 26 also rotates. In this example, tip member 14 is rotated approximately 90 degrees. This amount of rotation, however, is not intended to be limiting as the amount of rotation can vary. For example, control member 18 may be used to rotate tip member up to 360 degrees or more.

Figure 4:
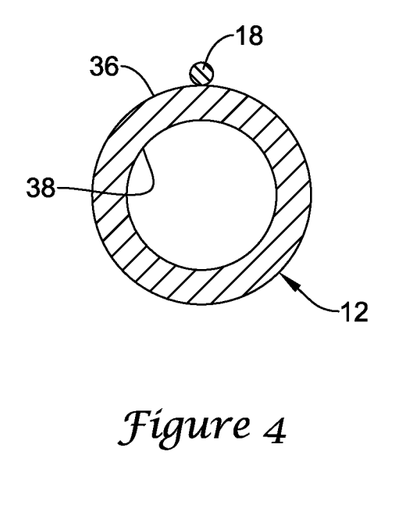
FIG. 4 is a cross-sectional view of a portion of an example catheter shaft where an example control member is disposed along the exterior of the catheter shaft.
Figure 5:
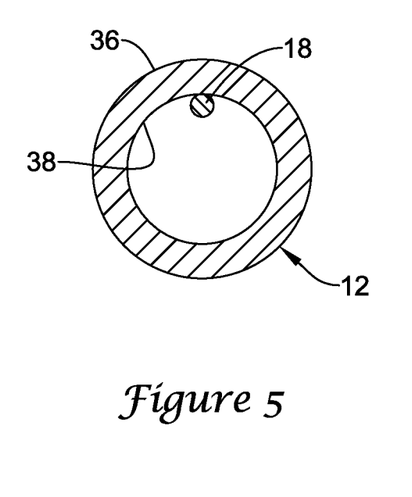
FIG. 5 is a cross-sectional view of a portion of an example catheter shaft where an example control member is disposed along the interior of the catheter shaft.
Figure 6:
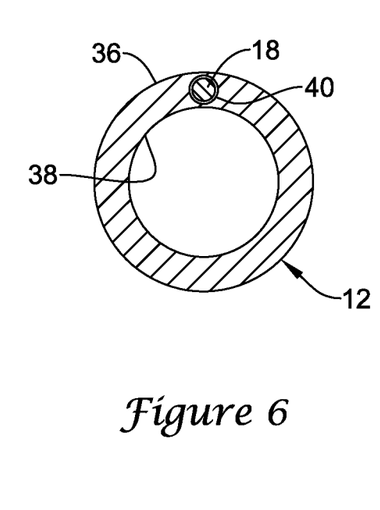
FIG. 6 is a cross-sectional view of a portion of an example catheter shaft where an example control member through a lumen formed in the wall of the catheter shaft.

Control member 18 may extend axially along catheter shaft 12 to the proximal end of catheter shaft 12. Here, a clinician may have access to control member 18, for example, directly or through a handle or other grasping structure. In some embodiments, control member 18 may extend to the proximal end of catheter shaft 12 via a sheath 22 (illustrated in FIG. 1) disposed along the exterior of catheter shaft 12. Sheath 22 may extend along the full length of catheter shaft 12 or, in other embodiments, sheath 22 may extend along only a portion of the length of catheter shaft 12 and then form a pathway into the interior of catheter shaft 12. Other embodiments are contemplated including those that do not utilize sheath 22. For example, control member 18 may extend along an exterior surface 36 of catheter shaft 12 as shown in FIG. 4. Alternatively, control member 18 may extend along an interior surface 38 of catheter shaft 12 as shown in FIG. 5. In still other embodiments, control member 18 may extend through a lumen 40 formed in the wall of catheter shaft 12 as shown in FIG. 6. As a further alternative, control member 18 may take the form of a filament or wire that only operates by pulling or retracting. In such an example, the tip may not need to be returned to its original position, or a spring may be used in the tip to allow for opposite rotation. These are just examples as other arrangements of control member 18 relative to catheter shaft 12 are contemplated including mixtures of these orientations as well as other orientations.

In some cases, the control member 18 may have a variable geometry along its length to increase its strength. For instance, the control member 18 may have a relatively large diameter for much of its length, inside a catheter lumen or wall, and may taper to a relatively small diameter at its distal end. Other geometries may be possible as well, including notches or grooves that may extend along the length of the control member.

Figure 7:
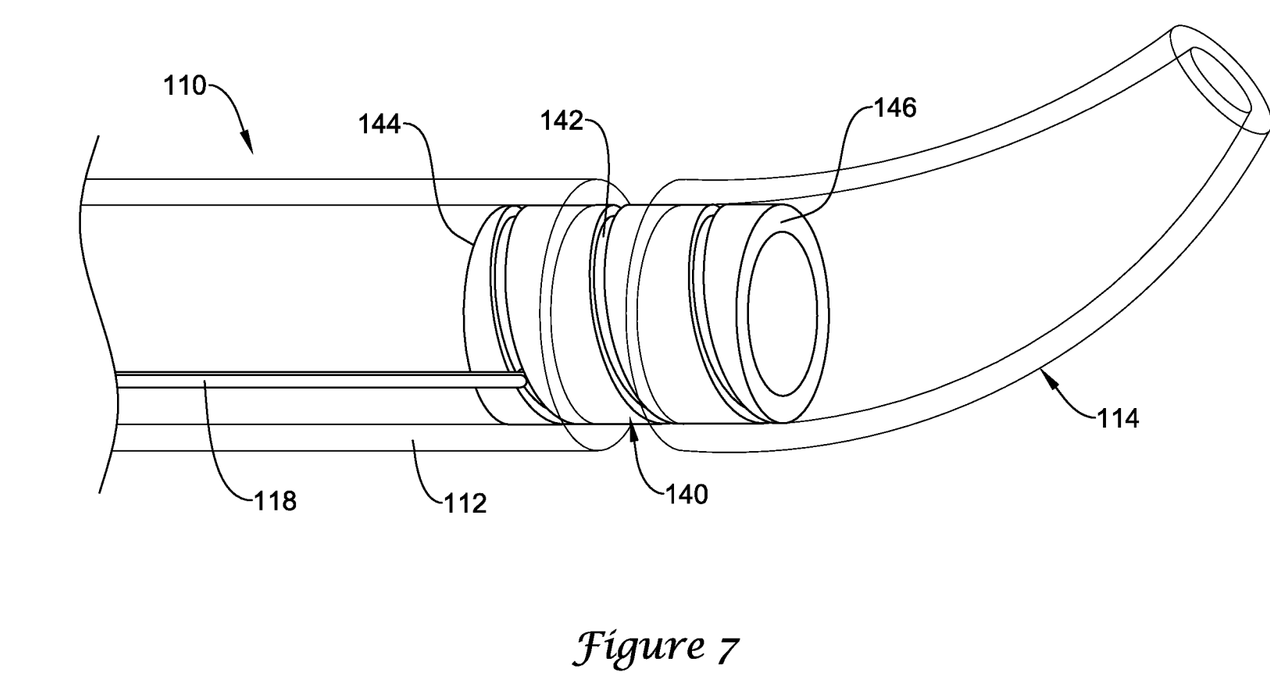
FIG. 7 is a side view of another example medical device.

FIG. 7 illustrates another example medical device 110, which may be similar in form and function to other medical devices disclosed herein. Device 110 may include catheter shaft 112 and tip member 114. In some cases, the tip may be bendable with a pull wire or steering wire. In at least some embodiments, tip member 114 is curved and/or bent. In general, the curved tip member 114 may be used to selectively guide another medical device to a target location in a manner similar to tip member 14. In other embodiments, tip member 114 may be configured similarly to tip member 14 and may function in a similar manner. A sleeve 140 may be attached to tip member 114. For example, a distal portion 146 of sleeve 140 may be attached to tip member 114 along a portion of the inner surface of tip member 114. Sleeve 140 may have a groove 142 formed therein that may be used in conjunction with control member 118 to rotate tip member 114. A proximal portion 144 of sleeve 140 may be disposed within catheter shaft 112 and form a junction or coupling with catheter shaft 112. Such a connection may include, for example, a mechanical bond or a swivel-type bond that secures sleeve 140 to catheter shaft 112 while permitting rotation of sleeve 140. Other bonds may also be utilized including a threaded connection between sleeve 140 and catheter shaft 112.

Figure 8:
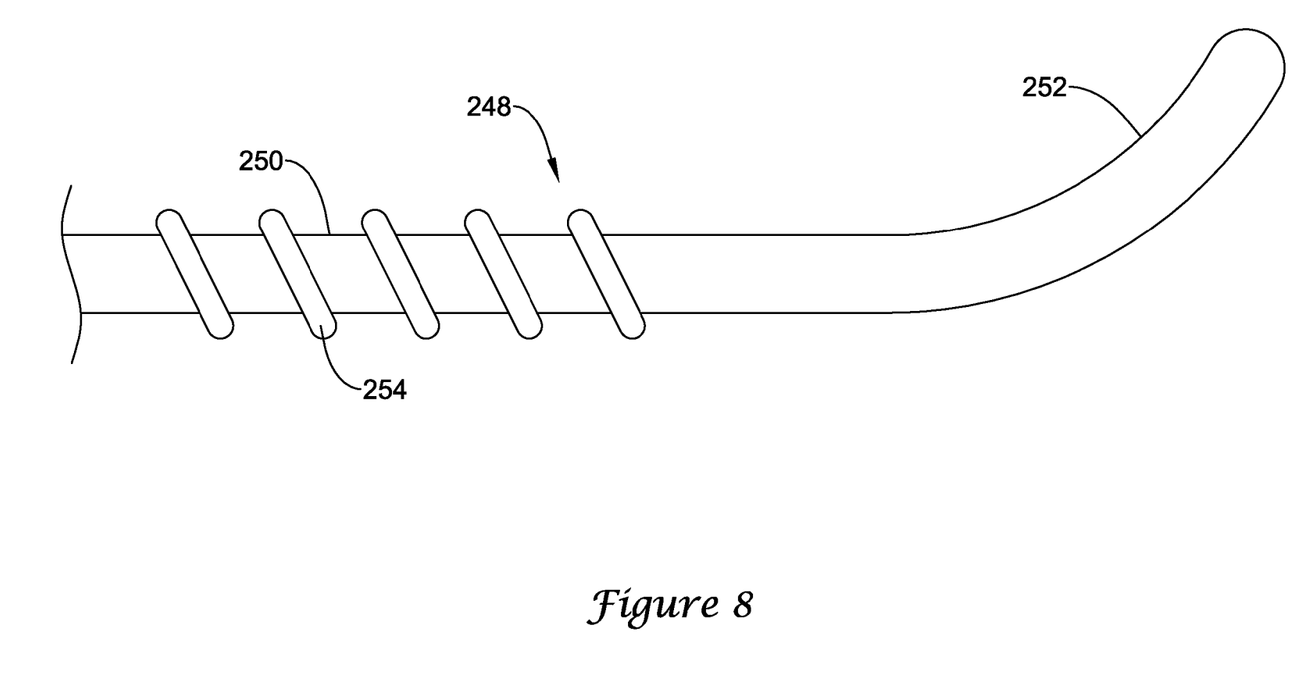
FIG. 8 is a side view of another example medical device.
Figure 9:
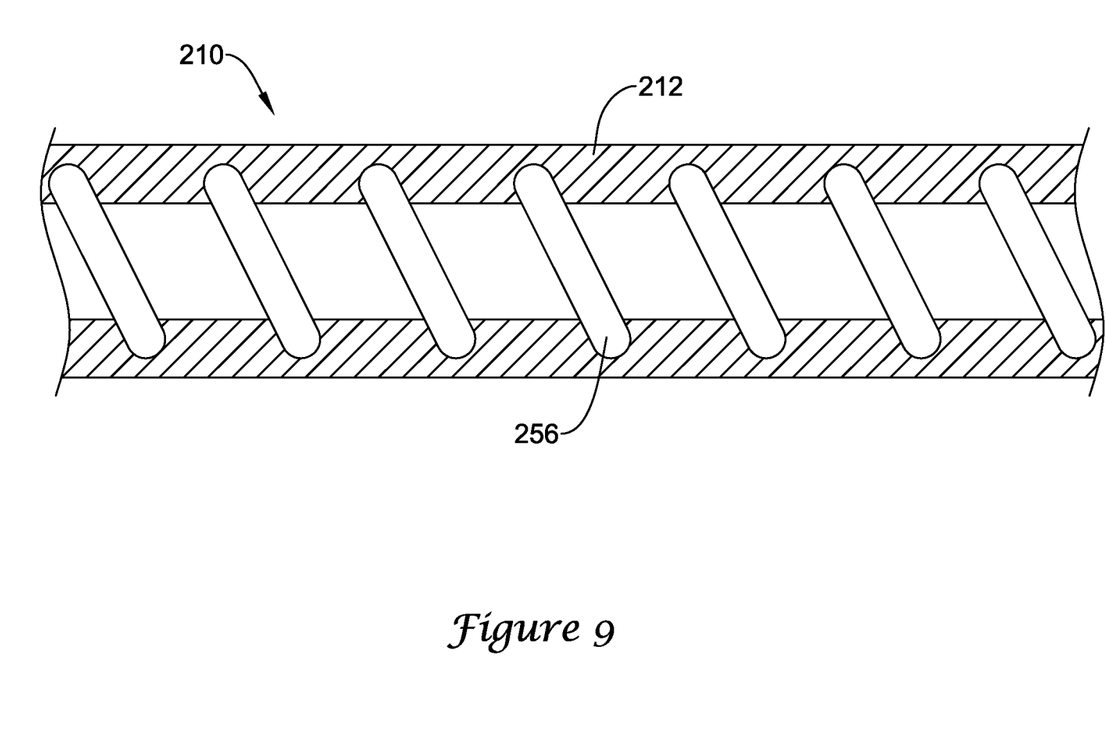
FIG. 9 is a cross-sectional side view of a catheter shaft for use with the medical device illustrated in FIG. 8.

While the forgoing discussion is related to the manipulation of a tip or tip member of a catheter in order to selectively guide another medical device into the desired target location, this is not intended to be limiting. For example, FIG. 8 illustrates another example medical device 248, which takes the form of a guidewire. Guidewire 248 may have a body portion 250 and a distal portion 252. Distal portion 252 may be curved. A thread 254 may be disposed along body portion 250. Thread 254 may be configured to aid in the rotation of guidewire 248. For example, guidewire 248 may be passed through an example catheter 210 that includes a catheter shaft 212 with a mating thread 256 formed therein (and/or other structures that may be configured to rotate or deflect guidewire 248) as shown in FIG. 9. Thus, as guidewire 248 is distally advanced or proximal retracted, the threaded relationship between guidewire 248 and catheter 210 causes guidewire 248 to rotate relative to catheter 210. It can be appreciated that the threaded relationship between catheter 210 and guidewire 248 causes guidewire 248 to rotate in one direction when guidewire 248 is distally advanced and in the opposite direction when guidewire 248 is proximally retracted. Thus, guidewire 248 can be advanced and/or retracted within catheter 210 so that the curved distal portion 252 of guidewire 248 is oriented in a direction that points toward the desired target site. In some embodiments, the end of one or both of the threads 254/256 may have a stop formed thereon that forms a physical barrier that stops rotation of catheter 210 beyond a certain point and, thus, limit further rotation.

Figure 10:
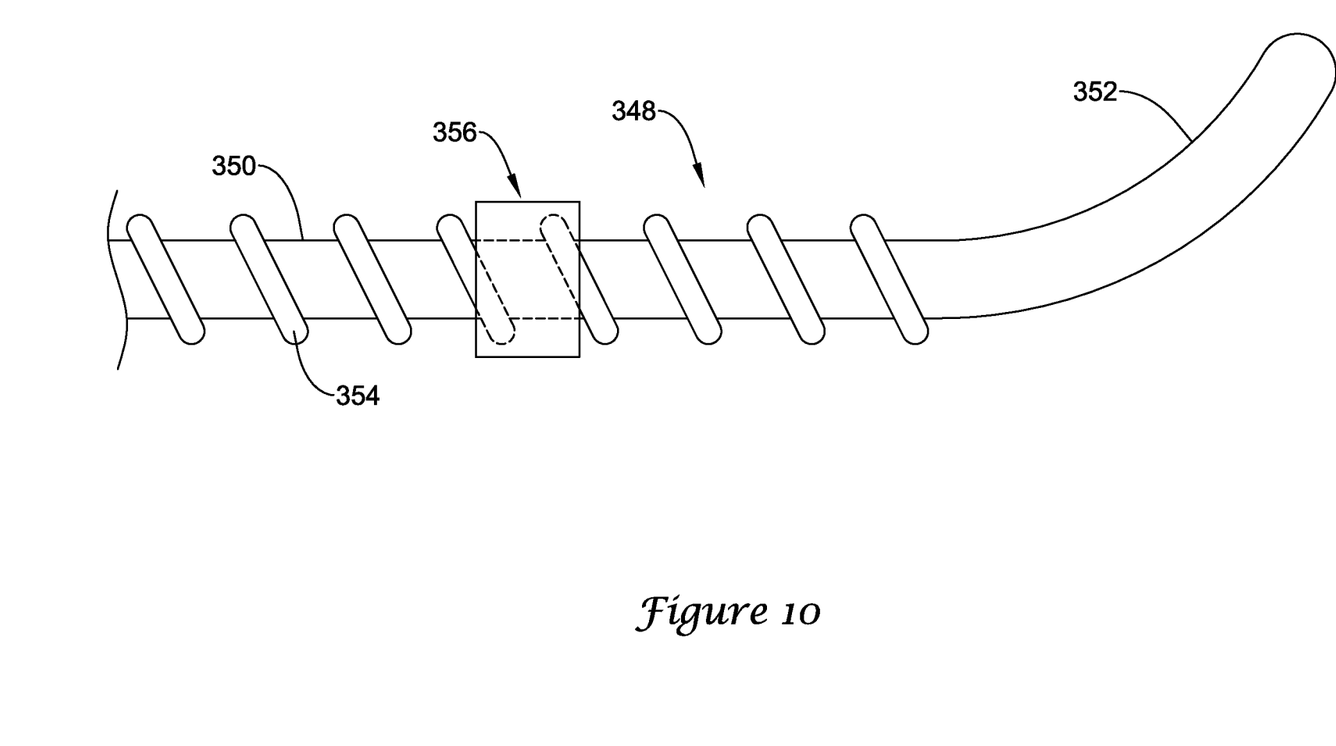
FIG. 10 is a side view of another example medical device.

FIG. 10 illustrates another example medical device 348. Much like guidewire 248, guidewire 348 has body portion 350, distal portion 352, and thread 354. In addition, guidewire 348 has a threaded clutch member 356 coupled thereto. For example, clutch member 356 may take the form of a ring structure with an internal thread that is configured to mate with thread 354. Clutch member 356 may be configured to aid in the rotation of guidewire 348. For example, clutch member 356 may be configured to be held stationary during an intervention so that movement of guidewire 348 and the threaded relationship between clutch member 356 and guidewire 348 causes guidewire 348 to rotate. In some embodiments, clutch member 356 may be similar to any of the example clutch structures disclosed in U.S. Pat. No. 7,758,591, the disclosure of which is incorporated by reference herein in its entirety.

Figure 11:
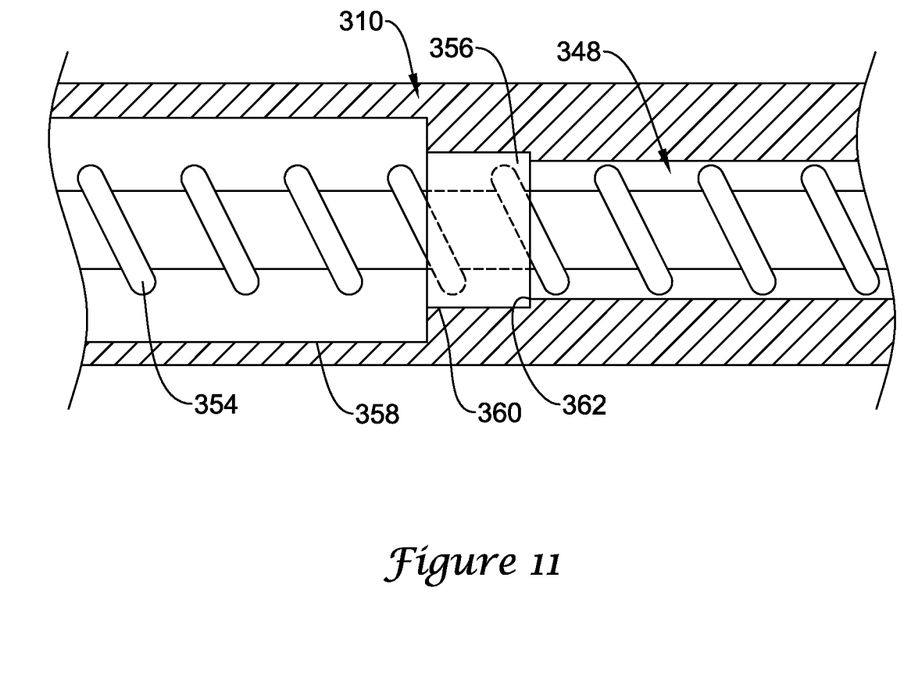
FIG. 11 is a partial cross-sectional side view of the medical device illustrated in FIG. 10 disposed within a first portion of an example catheter shaft.
Figure 12:
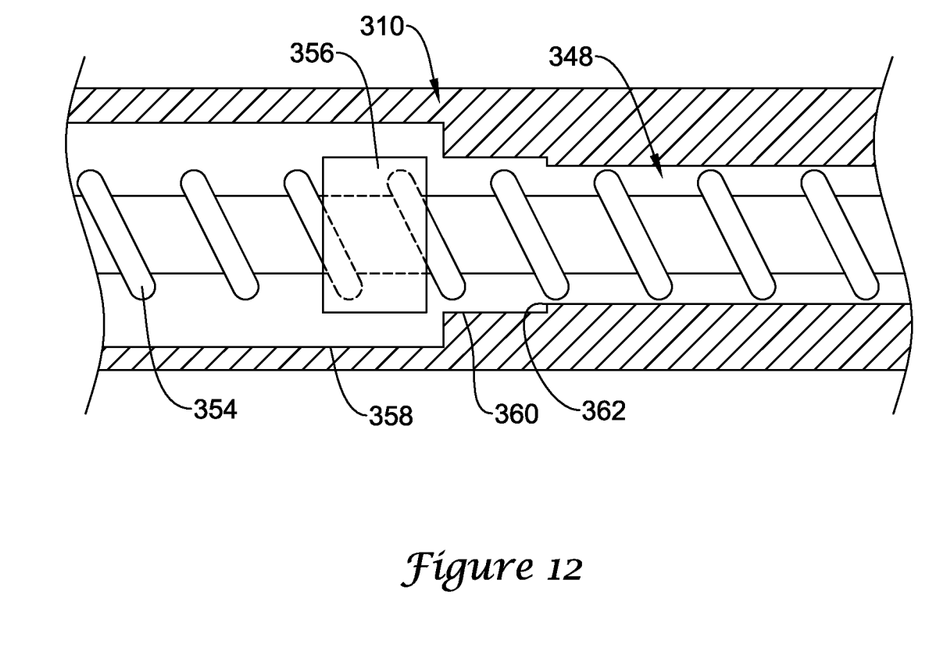
FIG. 12 is a partial cross-sectional side view of the medical device illustrated in FIG. 10 disposed within a second portion of the example catheter shaft.

As shown in FIG. 11, guidewire 348 may be advanced through catheter 310. Catheter 310 may have a proximal inner wall portion 358, a distal inner wall portion 360, and a distal ledge 362. When guidewire 348 is advanced distally within catheter 310, clutch member 356 may engage distal portion 360 and/or distal ledge 362 of catheter 310. Portion 360 and/or ledge 362 may limit further distal motion of clutch member 356. For example, portion 360 may have an inner diameter less than that of portion 358 so that portion 360 can frictionally engage clutch member 356 so as to prevent further distal movement and/or rotation of clutch member 356. Alternatively or in addition, distal ledge 362 may form a structural barrier that prevents further distal movement of clutch member 356. When guidewire 348 passes through portion 358, guidewire 348 is not forced to rotate within catheter 310. When guidewire 348 is advanced further in the distal direction, clutch member 356 engages portion 360 and/or ledge 362 so that the threaded relationship between clutch member 356 and guidewire 348 causes guidewire 348 to rotate therein. When guidewire 348 is proximally retracted, clutch member 356 disengages from portion 360 and/or ledge 362 and retracts to a position adjacent to portion 358 of catheter 310 as shown in FIG. 12. When so positioned, movement of guidewire 348 does not result in further rotation of guidewire 348. This allows the selective rotation of guidewire 348 only when guidewire 348 is advanced distally within catheter 310.

Figure 13:
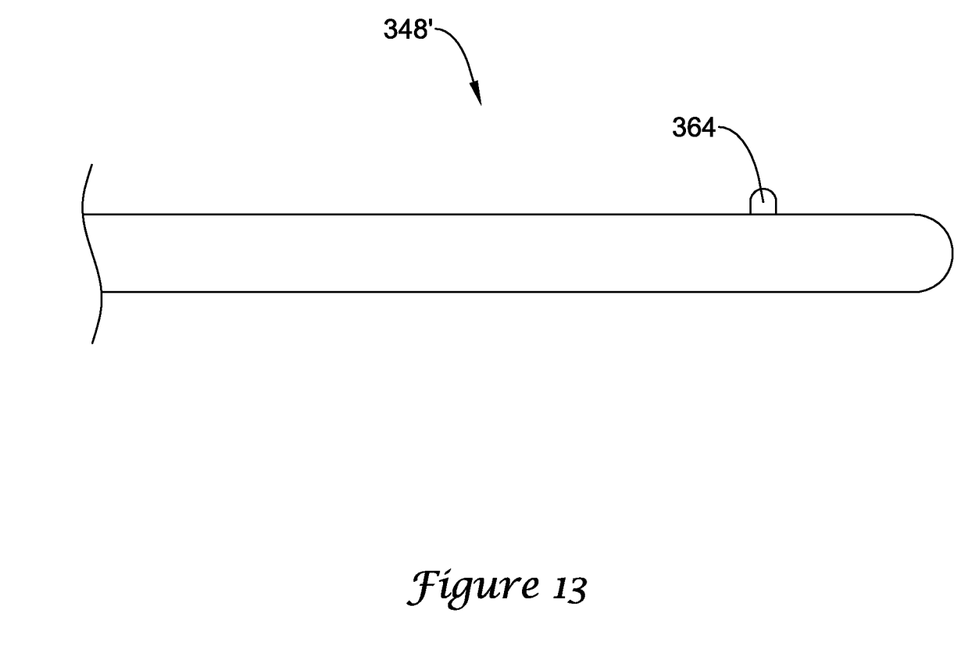
FIG. 13 is a side view of another example medical device.

Note that as an alternative, the exterior thread need not extend along the length of the guidewire 348, and may be replaced with a small tab 364 on the side of the guidewire 348' (illustrated in FIG. 13) that can engage the portion 360 and/or ledge 362 of catheter 310 to produce rotation. Likewise, the guidewire 348 may include a groove on its exterior, rather than a thread, and may engage a thread or tab inside the tip member.

The materials that can be used for the various components of the various devices disclosed herein may include those commonly associated with medical devices. For simplicity purposes, the following discussion makes reference to device 10 and catheter shaft 12. However, this is not intended to limit the devices and methods described herein, as the discussion may be applied to any of the other structures and/or components of the devices disclosed herein.

Catheter shaft 12 and/or other components of device 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Catheter shaft 12 and/or other components of device 10 may include support and/or reinforcing structures incorporated therein such as, for example, a braid, a coil, a mesh, supporting fillers or amalgams, or the like. In addition, catheter shaft 12 and/or other components of device 10 may include cuts, slots, holes, openings, or the like formed therein, which may increase the flexibility.

In at least some embodiments, portions or all of catheter shaft 12 and/or other components of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of Magnetic Resonance Imaging (MRI) compatibility is imparted into device 10. For example, to enhance compatibility with MRI machines, it may be desirable to make catheter shaft 12, or other portions of device 10, in a manner that would impart a degree of MRI compatibility. For example, catheter shaft 12, or portions thereof, may be made of a material that does not substantially distort the image and create substantial artifacts (i.e., gaps in the image). Certain ferromagnetic materials, for example, may not be suitable because they may create artifacts in an MRI image. Catheter shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

As indicated above, catheter shaft 12 and/or other component the medical device 10 may be made from or otherwise include a polymer or polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

In some embodiments, the exterior surface of device 10 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of device 10. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), gradient extrusion, or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device, comprising:
   an elongate catheter shaft having a distal end;
   a tip member rotatably coupled to the distal end of the catheter shaft, the tip member having a groove extending along a portion of the circumference of the tip member; and
   a control member coupled to the catheter shaft, the control member being configured to slidingly engage the groove and rotate the tip member relative to the catheter shaft such that the tip member rotates relative to the control member;
   wherein axial translation of the control member rotates the tip member when the control member is slidingly engaged with the groove.

2. The medical device of claim 1, wherein the groove in the tip member is helical.

3. The medical device of claim 1, wherein the tip member has a distal opening formed therein that is disposed at an angle relative to a longitudinal axis of the catheter shaft.

4. The medical device of claim 1, wherein the tip member is curved.

5. The medical device of claim 1, wherein the tip member is steerable.

6. The medical device of claim 1, wherein the control member includes a control wire.

7. The medical device of claim 6, wherein the control wire extends through a wall lumen formed in a wall of the catheter shaft.

8. The medical device of claim 6, wherein the control wire extends along an exterior wall surface of the catheter shaft.

9. The medical device of claim 6, wherein the control wire extends along an interior wall surface of the catheter shaft.

10. The medical device of claim 9, further comprising a sheath disposed along the exterior wall surface of the catheter shaft, the control wire extending within the sheath.

11. The medical device of claim 1, wherein the groove is formed along an exterior surface of the tip member.

12. The medical device of claim 1, wherein the groove is formed along an interior surface of the tip member.

13. A method for performing a medical procedure, the method comprising:
   providing a catheter, the catheter comprising:
      an elongate catheter shaft having a distal end;
      a tip member rotatably coupled to the distal end of the catheter shaft and having a groove extending along a portion of the circumference of the tip member, and
      a control wire engaged with the groove and configured to rotate the tip member relative to the control wire;
   advancing the catheter through a body lumen to a position adjacent to a target region; and
   rotating the tip member relative to the catheter shaft by actuating the control wire.

* * * * *